(12) United States Patent
Castellacci

(10) Patent No.: US 6,827,692 B2
(45) Date of Patent: Dec. 7, 2004

(54) NEEDLE OF THE BIOPSY TYPE OR FOR TAKING OTHER SAMPLES FROM HUMAN OR ANIMAL ORGANS

(76) Inventor: Pietro Castellacci, Via A. M. Bandini 3, 50134 Firenze (IT)

( * ) Notice: Subject to any disclaimer, the term of this patent is extended or adjusted under 35 U.S.C. 154(b) by 289 days.

(21) Appl. No.: 10/088,936

(22) PCT Filed: Jul. 19, 2001

(86) PCT No.: PCT/IT01/00387

§ 371 (c)(1), (2), (4) Date: Mar. 21, 2002

(87) PCT Pub. No.: WO02/07603

PCT Pub. Date: Jan. 31, 2002

(65) Prior Publication Data

US 2002/0151821 A1 Oct. 17, 2002

(30) Foreign Application Priority Data

Jul. 24, 2000 (IT) ................................. FI2000A0168

(51) Int. Cl.$^7$ ............................................ A61B 10/00
(52) U.S. Cl. ...................... 600/567; 600/564; 606/167
(58) Field of Search ......................... 600/562, 564–567; 606/167, 170

(56) References Cited

U.S. PATENT DOCUMENTS

| | | | | |
|---|---|---|---|---|
| 4,651,752 A | * | 3/1987 | Fuerst ....................... 600/567 |
| 4,785,826 A | | 11/1988 | Ward |
| 4,926,877 A | | 5/1990 | Bookwalter |
| 5,595,186 A | * | 1/1997 | Rubinstein et al. .......... 600/567 |
| 5,827,305 A | * | 10/1998 | Gordon ....................... 606/159 |
| 5,910,121 A | * | 6/1999 | Paolo et al. ................. 600/562 |
| 6,063,037 A | * | 5/2000 | Mittermeier et al. ........ 600/567 |
| 6,416,484 B1 | * | 7/2002 | Miller et al. ................ 600/564 |

FOREIGN PATENT DOCUMENTS

| EP | 0 852 127 A1 | 7/1998 |
|---|---|---|
| SU | 1537232 | 1/1990 |

* cited by examiner

Primary Examiner—Charles Marmor
(74) Attorney, Agent, or Firm—McGlew and Tuttle, P.C.

(57) ABSTRACT

A needle has an external cannula (1) and a closing stem (3). The cannula (1) has one portion of relatively small thickness (s) and one portion, set at the mouth (1B) of the needle, of a larger thickness (s1), the two portions of different thickness being separated by an internal edge (1D) developed according to plane (W) inclined with respect to the axis (X—X) of the cannula. Inserted between the cannula (1) and the stem (3) is a tubular element (5), which can slide axially and which can be controlled independently, the tubular element (5) having one end provided with a tabe-like extension (5C) designed to engage with the inclined edge (1D) so as to undergo deflection in order to close the mouth of the cannula (1).

11 Claims, 4 Drawing Sheets

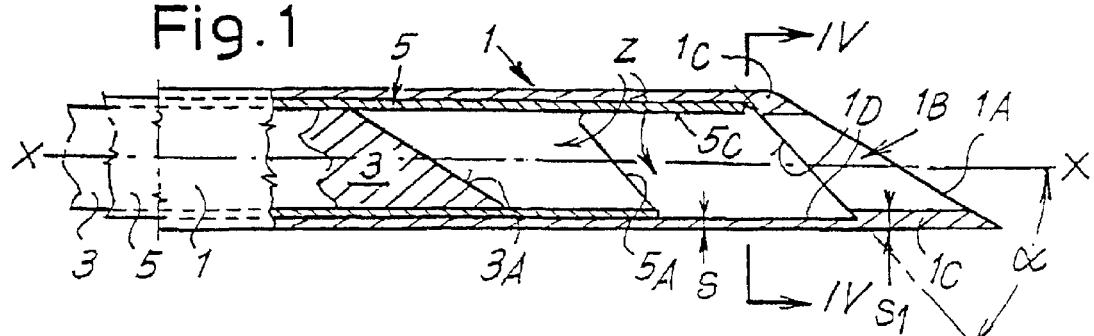
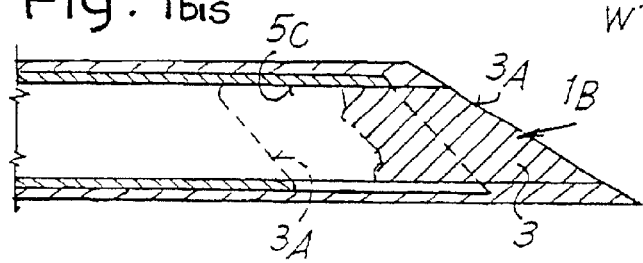
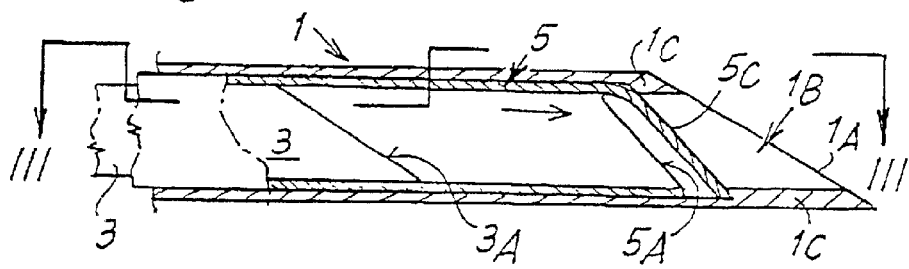
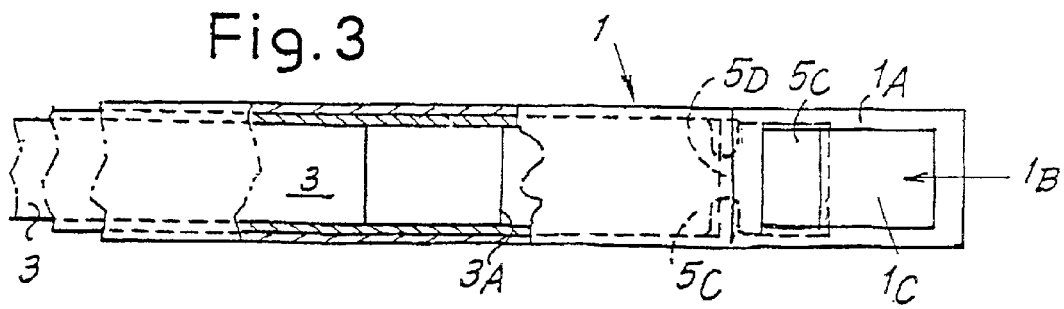
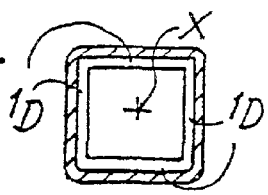

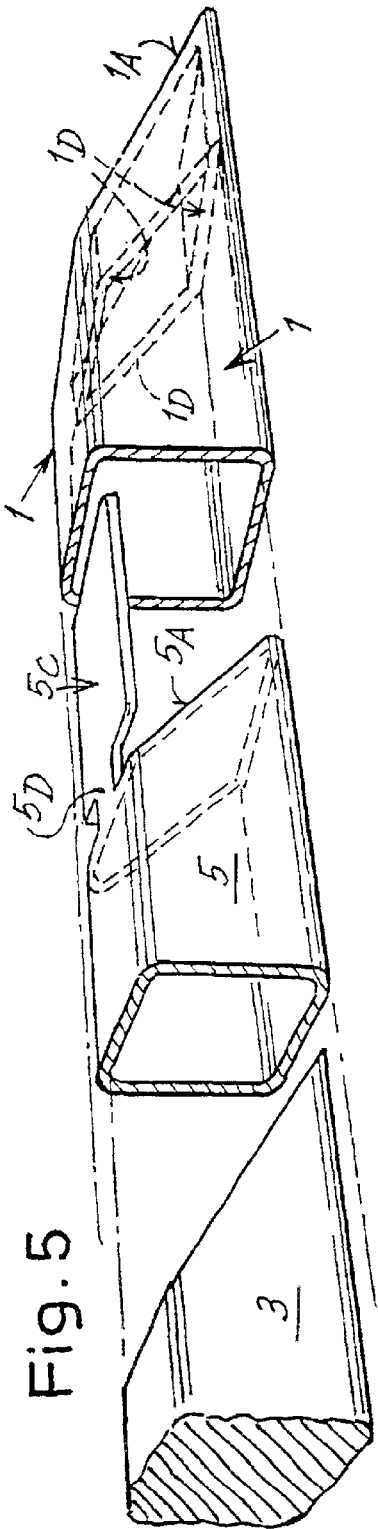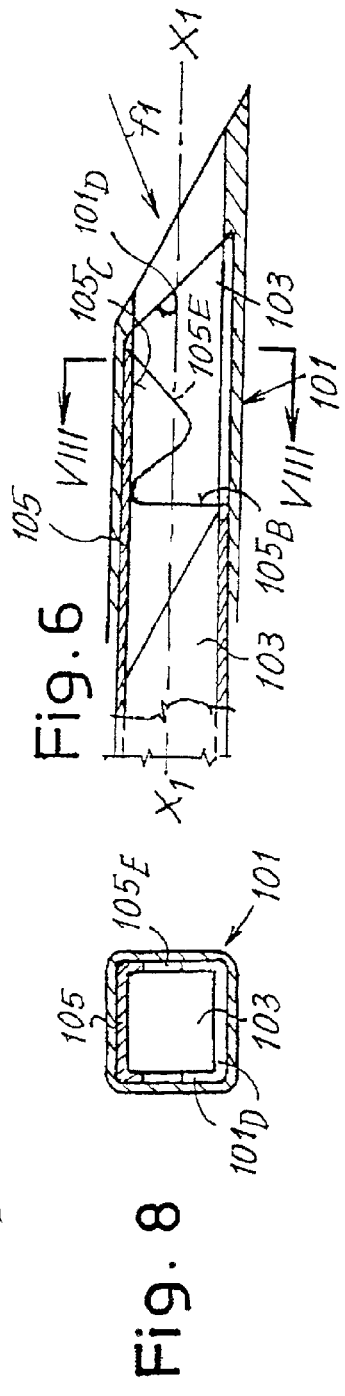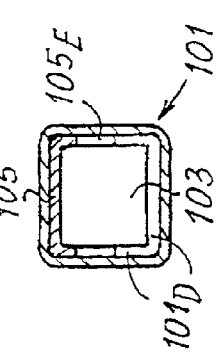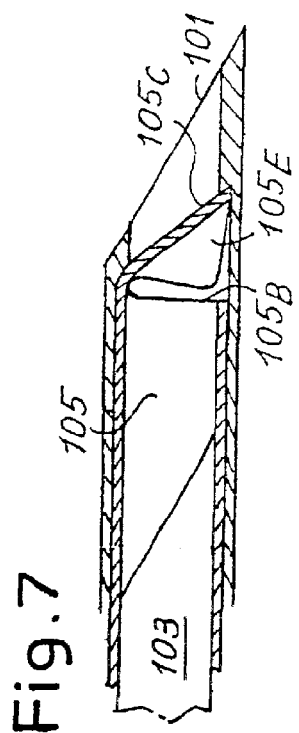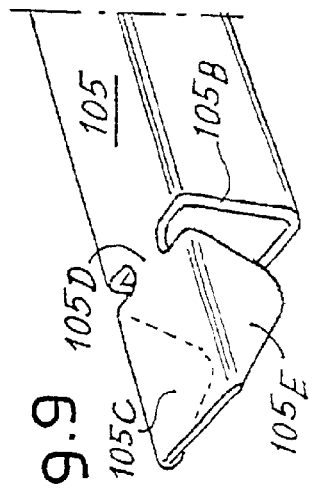

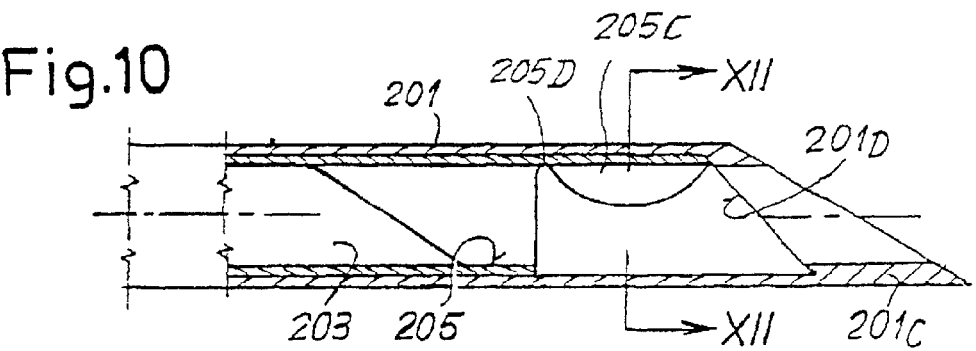
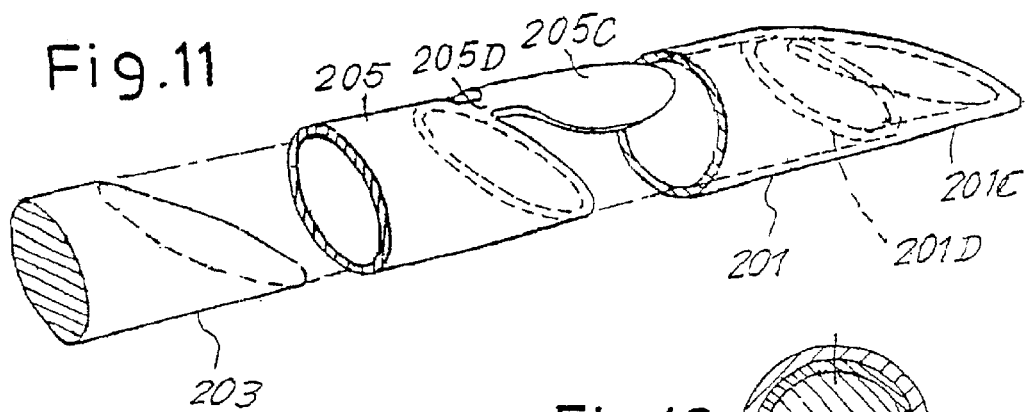
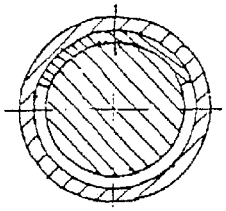
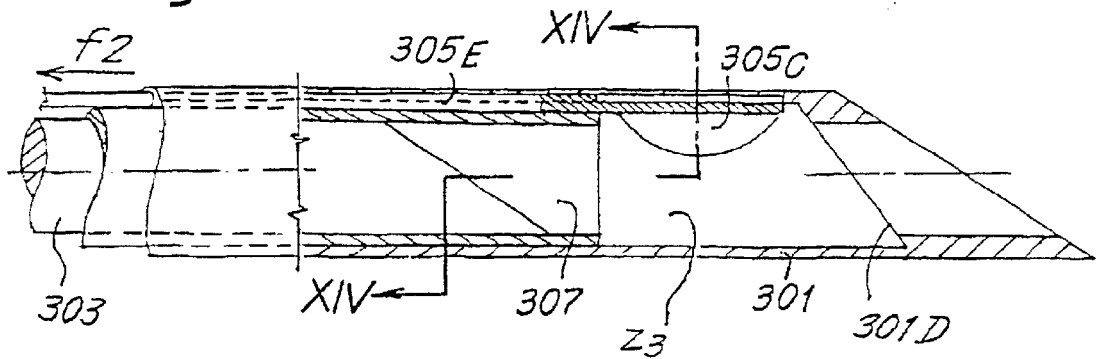
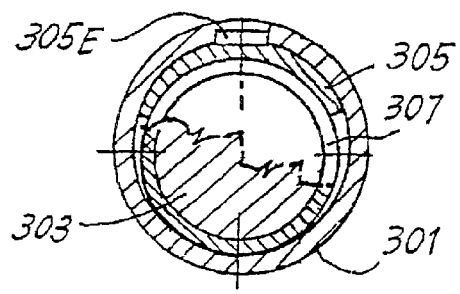

NEEDLE OF THE BIOPSY TYPE OR FOR TAKING OTHER SAMPLES FROM HUMAN OR ANIMAL ORGANS

CROSS REFERENCE TO RELATED APPLICATIONS

This application claims the benefit of priority under 35 U.S.C. § 119 of filed PCT/IT01/00387, the entire contents of which are incorporated herein by reference.

FIELD OF THE INVENTION

The present invention relates to a needle of the biopsy type or for taking other samples from human or animal organs. In general, such needles comprise an external cannula and a stem that can slide within the cannula and can be controlled independently of the latter. The cannula has one end fixed to a manipulating element, whilst the other end is tapered or beveled, with a sharp edged mouth designed to penetrate into tissue. The stem with its end that is distal with respect to the grip is designed to close: the mouth of the cannula from inside. The stem moreover has a recessed area developed for a certain stretch in the vicinity of the aforesaid end in order to contain a specimen of tissue taken from the organ concerned by means of a well-known manipulation technique.

BACKGROUND OF THE INVENTION

The aforesaid needles present the drawback that the amount of tissue, sampled is small in so far as the aforementioned recessed area occupies only one part of the section of the stem, in general one half. Consequently, in order to take a sufficient amount of tissue, it is necessary to use a needle of considerable thickness. In addition, the tissue, which in general has a gelatinous consistency may easily get lost or contaminated during manipulation of the elements of the needle.

The document SU 1537232 describes a biopsy needle comprising an external cannula having a rectangular cross section, and a flexible closing element, which can slide inside the cannula. At a point corresponding to the tip of the cannula, the latter has lateral guide grooves in which said closing element engages, so as to be deflected and thus close the opening of the needle both to enable the first step of penetration of the needle into the body of the patient without collecting any material and to enclose a specimen of tissue before extraction of the needle. The above conformation does not, however, afford the possibility of extracting the tissue specimen from the needle while still leaving the external cannula of the needle itself in situ in the body of the patient, for checking the quality of the tissue sampled and possibly repeating the sampling operation at a greater depth.

SUMMARY OF THE INVENTION

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

One purpose of the present invention is to overcome the above-mentioned drawbacks; other advantages will emerge from the ensuing description and claims.

A biopsy needle according to the invention comprises a cannula with a sharpened front end that is tapered or beveled, and a stem designed to close the mouth of the cannula in a known way. The cannula has, for a certain stretch in the vicinity of the mouth, a first portion of relatively small thickness and a second portion in an area corresponding to the mouth of a larger thickness, the two portions forming between them, inside the cannula, a step-like, portion developed according to an inclined plane with respect to the axis of the cannula. Between the cannula and the stem there is inserted an axially slidable element for withholding the tissue specimen, said slidable element being controllable independently of the stem and of the cannula. Said element has, in the vicinity of said internal step-like portion of the cannula, an end provided with a tab-like extension which, by means of the relative sliding between the slidable element and the cannula and in the direction of the mouth of the latter, is designed to engage at the front with the step-like portion in order to bend, so closing the, mouth of the cannula, thus cutting the tissue specimen that is being sampled and withholding it inside the withholding element during extraction of the latter and ,possibly also of the needle. In this way, the specimen has a right cross section equal to that of the mouth of the cannula and is withheld securely inside the latter both during extraction of the needle from the organ concerned and afterwards. The tab like extension preferably has a restricted area of connection with the withholding element in order to facilitate bending thereof, the said bending occurring beyond the elastic limit of the tab itself and thus generally being permanent.

In a particular embodiment of the invention, the tab-like extension (tab extension) has side walls that are designed to contain the tissue specimen laterally.

The external cannula may have a polygonal cross section, for example a square cross section, or even a circular or elliptical cross section.

The arrangement according to the invention can be applied, both to needles for taking samples of soft tissue and to needles for taking intraosseous samples.

In particular embodiments of the invention, there may be provided, between the withholding element and the stem for closing the needle, a further axially slidable element, generally of a tubular shape. This additional element is configured so that it can be set in contrast with said tab extension of the withholding element, once the tab extension is bent, then to re-open the tab extension in the specimen-extraction step, so as to facilitate extraction of the tissue specimen without damaging it, as will be described in greater detail in what follows.

BRIEF DESCRIPTION OF THE DRAWINGS

A better understanding of the present invention will be provided by the ensuing description and by the attached drawings, which illustrate non-limiting examples of the invention. In the drawings:

FIGS. 1, 1bis and 2 are partial side views of a biopsy needle according to the invention; with the components of the needle in two different arrangements;

FIGS. 3 and 4 respectively illustrate a view of the needle taken according to the plane indicated by III—III in FIG. 2 and a cross section of the needle taken according to the plane indicated by IV—IV in FIG. 1;

FIG. 5 is an exploded perspective partial view of the needle of FIG. 1;

FIGS. 6 and 7 are views similar to those of FIG. 1 and FIG. 2 of a biopsy needle according to another embodiment of the invention;

FIG. 8 is a cross-sectional view according to the plane indicated by VIII—VIII of FIG. 6;

FIG. 9 is a perspective view of an element of the needle, according to the arrow F1 of FIG. 6;

FIGS. 10, 11 and 12 are views similar to those of FIGS. 1, 5 and 4, respectively, according to another embodiment of the invention;

FIGS. 13, 14 and 15 are views similar to those of FIGS. 1, 4 and 2, respectively, according to a further embodiment of the invention;

DESCRIPTION OF THE PREFERRED EMBODIMENT

Figure 15:
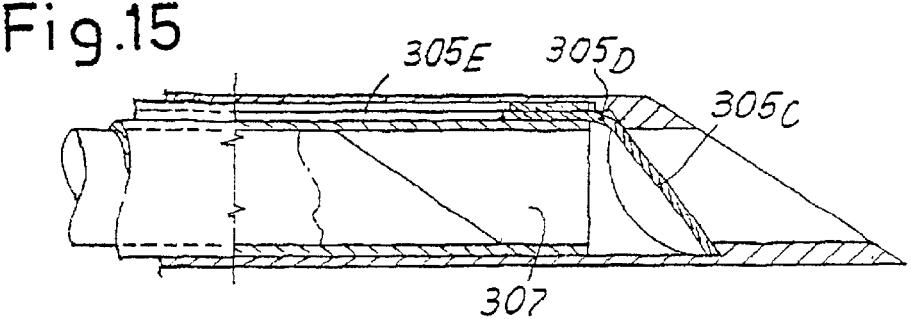
Figure 16:
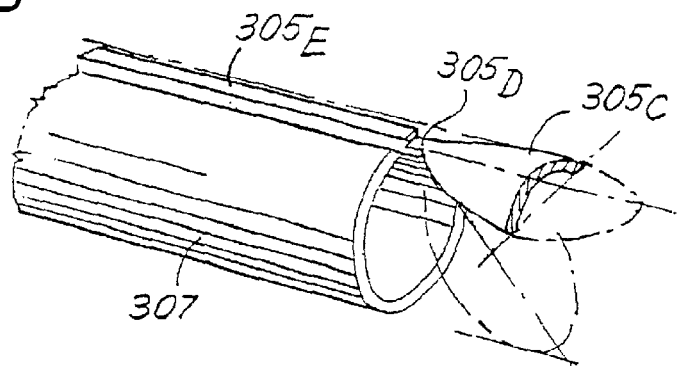
FIG. 16 is a partial perspective view of elements of the needle of FIG. 13.

With reference to FIGS. 1 to 5, the needle comprises an external cannula 1 of square cross section, one end of which (not illustrated in the drawing) is fixed to a manipulation element, such as a grip, whilst the other end 1A is shaped so that it is inclined, tapered or beveled and has a mouth 1B with its edges sharpened for penetrating into the tissue. The needle also comprises a stem 3, which can slide inside the cannula, and the end 3A of which (visible in the drawing) is also shaped with a taper or bevel and has the same inclination as the end 1A of the cannula 1 and a cross section designed to penetrate with minimal play into the mouth 1B of the cannula 1 so as to close it. The stem 3 is controllable independently of the cannula 1 so that it can be displaced from one completely advanced closing arrangement (FIG. 1 bis), in which the inclined face 3A of the stem is flush with the face 1A of the mouth of the cannula, and a second arrangement, illustrated in FIG. 1, in which the stem 3 is retracted, and the face 3A defines, in the cannula 1, a chamber Z (see FIG. 1) designed to contain a tissue specimen that is to be sampled. The cannula 1 has, at least in the stretch shown in the drawing, a uniform thickness (s) of wall, except for one thicker portion 1C having a thickness (s1) in an area corresponding to the mouth 1B. Said thicker portion is delimited, towards the inside of the needle, by a plane W inclined at approximately 45° with respect to the axis X—X of the needle. Said plane W defines an internal edge 1D which forms a step that separates the two areas of different thickness of the cannula 1 from one another. Between the cannula 1 and the stem 3 there is inserted a withholding element 5 of a tubular shape and having a square cross section, said withholding element being axially slidable both inside the external cannula 1 and about the stem 3. The tubular element 5 is controllable independently of the stem 3 and of the cannula 1 for axial sliding and has one end 5A—set facing the mouth 1B of the cannula 1 shaped with a taper or bevel with the same inclination as the plane W. Said end 5A is provided at the top (see FIGS. 1 and 2) with a tab-like extension 5C. The tab-like extension (tab extension or extension) 5C slides laterally with minimal play inside the cannula 1 and is connected to the tubular element 5 by means of a stretch 5D of reduced width (see FIG. 5) so as to be easily bendable with respect to the element 5 itself.

Operation of the needle is described in what follows. The components of the needle are set together in one first penetration arrangement (FIG. 1bis) designed to bring the needle up to the tissue to be sampled. In this arrangement, the external cannula 1 and the tubular element 5 are positioned, with respect to one another, as shown in FIG. 1, i.e., with the tab extension 5C brought up to the wall of the cannula 1 and moved away from the thicker side 1C with respect to the free section of the mouth 1B. In this arrangement the stem 3, unlike in the case illustrated in FIG. 1, is in a position for closing the mouth 1B, with its own face 3A flush with the face 1A of the cannula. Once the needle has been made to penetrate, in this first arrangement, up to the tissue to be sampled, the stem 3 is drawn back with respect to the other components of the needle in order to form the chamber Z in the front part of the cannula 1, the components being arranged with respect to one another according a second arrangement of penetration illustrated in FIG. 1. The needle is made to advance, in this second arrangement, into the tissue that is to be sampled, where the mouth 1B of the cannula, with its own cutting edges, cuts a specimen from the tissue, said specimen entering the chamber Z. Once advance of the cannula 1 is completed, the element 5 is made to advance with respect to the cannula 1. In this movement, the front edge of the tab extension 5C slides on the edges 1D inclined according to the plane W and undergoes deflection in the thinned portion 5D, bending generally in a permanent way and enclosing, within the end of the element 5 itself, the majority of the tissue specimen that was in the chamber Z. The elements of the needle have thus now reached an extraction arrangement (FIG. 2), and the needle can be extracted from the patient, and the specimen can be easily discharged by extracting the stem 3 and the tubular element 5 from the cannula 1. Since the thickness 1C of the mouth of the cannula 1, albeit greater than that of the remaining part of the cannula, is relatively small if compared to the thickness of the needle, it follows that the cross section of the specimen, which corresponds to the cross section of the mouth 1B, is very close to the total section of the needle, so enabling use of needles of small thickness as compared to traditional needles.

According to a second embodiment of the invention, the needle has an external cannula 101 (FIGS. 6 to 8) whose internal edge 101D forms a stop analogous to 1D of FIGS. 1, 4 and 5, and an internal stem 103, which are similar to the analogous components illustrated in FIG. 1. An intermediate tubular element 105 is provided which, unlike the analogous component 5 of FIG. 1, has its front end 105B cut at right angles to the axis X1—X1. The intermediate tubular element 105 is provided with a front tab 105C which has a thinned portion 105D (see FIG. 9) to facilitate bending thereof, as in the previous case, and two side flaps 105E designed to enclose the specimen laterally so as to facilitate extraction of the latter from the cannula 101.

FIGS. 10, 11 and 12 show a biopsy needle according to another embodiment of the invention. The needle has a circular cross section and, otherwise, is altogether similar to the needle shown in FIGS. 1, 4 and 5. Also in this case, the external cannula 201 has its front part 201C which is thickened and forms an internal step 201D according to an inclined plane, where the inclination is approximately 45° with respect to the axis of the needle. Moreover provided are a closing stem 203, designed to close the mouth of the needle during penetration of the latter into the body of the patient, and a withholding element 205 having a tubular shape and being provided with a tab-like extension 205C, which is tile-shaped according to an elliptical plan and is connected to the element 205 by means of a restricted part 205D. Operation of this needle is altogether similar to that of the needle of FIG. 1.

FIGS. 13, 14, 15 and 16 show a biopsy needle according to another embodiment of the invention, which is on the whole similar to the one shown in FIG. 10 with a stem 303 analogous to 203 of FIG. 10. In the present case, the tab 305 is carried through a thinned portion 305D analogous to 205D of FIG. 11 by a rectilinear stem 305E which has a rectangular cross section and is guided so that it can slide between a corresponding internal slot of the cannula 301 and a tubular element 307, which is also axially slidable. The tubular element 307 has, in the direction of the tab 305C, an end truncated at right angles with respect to the axis of the needle. Once the specimen that is being taken has entered the cavity Z3 by means of manoeuvres of the type already described in the previous cases, and once the stem 305E has been made to advance towards the tip of the cannula, bending the tab 305C against the inclined plane 301D for withholding the specimen, and finally once the needle has been extracted from the body of the patient, the arrangement described enables re-opening of the tab 305C by pulling the stem 305E in the direction indicated by the arrow F2 and by pushing against the end of the tubular element 307. Opening of the tab 305C can therefore take place without interfering with the specimen, and hence preventing any possibility of the latter getting damaged. The above arrangement is particularly suited for taking samples of soft, semi-gelatinous, tissue.

Figure 17:
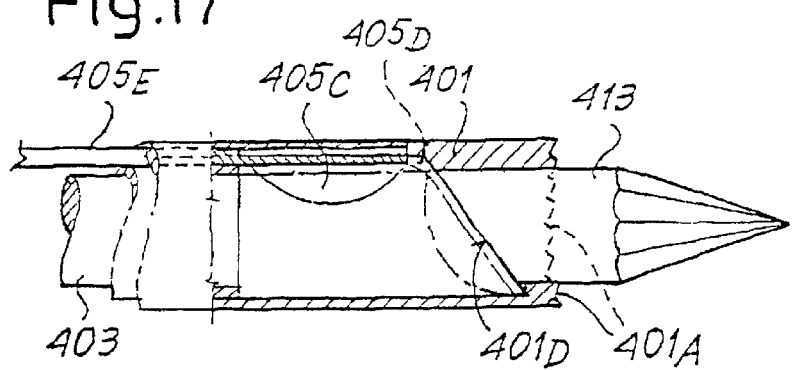
FIGS. 17 and 18 illustrate views of a biopsy needle, axially sectioned, according to yet another embodiment of the invention and in different arrangements of the component elements.
Figure 18:
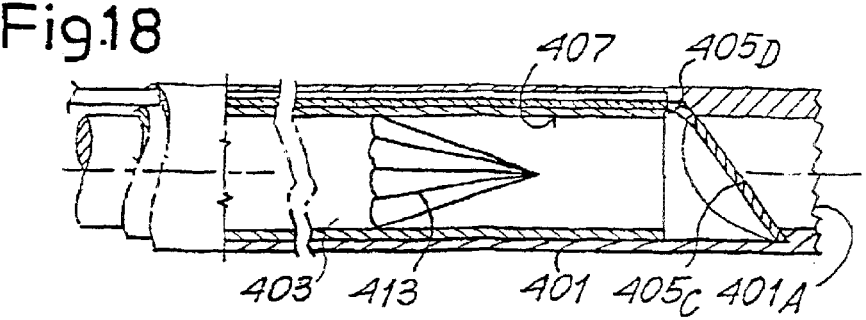

FIGS. 17 and 18 illustrate a needle according to a further embodiment of the invention, which is particularly suited for taking bone-marrow samples. The needle has an external cannula 401, the end 401A of which is truncated at right angles with respect to the axis of the cannula and is serrated at the front, and a closing stem 403, the end of which is shaped so that it has a faceted tip 413. For penetration, the needle is set in the arrangement illustrated in FIG. 17, and when it encounters osseous parts, it can be made to rotate about its own axis. The needle also comprises a tab 405C, that, by means of a thinned portion 405D analogous to 105D, 205D, 305D of the example shown, is connected to a stem 405E analogous to 305E of FIGS. 14 to 16. Said tab 405C co-operates with an internal step 401D of the cannula 401, and a tubular element 407 for reopening the tab 405C in a way similar to the one described for the needle illustrated in FIG. 13.

For extraction of the specimen from the cannula of the needle, it is possible to resort to a pushing means after prior re-opening of the withholding tab. Alternatively, it is possible to proceed with, a system of extraction by aspiration, i.e., by suction pressure, from behind the tip 1A of the needle. In this case, a vacuum source is connected to a closed element for collecting the specimen, and from this element a suction pipe is connected to the end of the needle opposite to the tip 1A that is shaped with a bevel or taper. When the vacuum source is opened, the specimen is sucked in and collected in the aforesaid closed element.

Before penetration of the needle into the tissue, the cannula 1 may be coated with a sheath—made of a synthetic resin, such as Teflon® or the like having a sufficient consistency for it to remain in the tissue without collapsing after extraction of the needle. In this way, haemorrhage can be prevented, and an access is maintained for draining, medication, topical treatment, or other operations. Subsequently, using substances of a collagen type, it is possible to proceed to plugging the access cavity and to extracting said sheath.

It is understood that the drawings only illustrate a possible exemplification of the invention given purely to provide a practical demonstration of said invention, which may vary in its embodiments and arrangements without thereby departing from the scope of the underlying idea. The possible presence of reference numbers in the attached claims has the purpose of facilitating reading thereof in the light of the foregoing description and in no way limits the scope of protection represented by the claims.

While specific embodiments of the invention have been shown and described in detail to illustrate the application of the principles of the invention, it will be understood that the invention may be embodied otherwise without departing from such principles.

What is claimed is:

1. A biopsy needle, comprising an external cannula and a closing stem adapted to slide inside the cannula, wherein the cannula has, in the vicinity of an opening, one portion having a relatively small thickness and one portion of larger thickness set at a penetrating mouth of the cannula, the two portions of cannula of different thickness forming together a step set inside the cannula and developed along a plane inclined with respect to an axis of the cannula; and wherein inserted between the cannula and the stem is a withholding element adapted to slide axially independently of the stem and of the cannula, and which has, in the vicinity of the mouth of the cannula, one end provided with an extension said extension sliding with respect to the cannula and in the direction of the mouth of the cannula, said extension designed to engage with said inclined step and to undergo deflection so as to close the mouth of the cannula and to withhold a tissue specimen inside the needle.

2. The biopsy needle according, to claim 1, wherein said extension has a restricted region for connection with the withholding element so as to facilitate said deflection.

3. The biopsy needle according to claim 2, wherein said extension has side walls designed to contain the tissue specimen laterally.

4. The biopsy needle according to claim 2, further comprising a sliding element designed to be set in contrast with the extension to re-open said extension so as to facilitate extraction of the tissue specimen without damaging the specimen.

5. The biopsy needle according to claim 1, wherein said deflection of said extension takes place beyond the elastic limit of the latter and is generally permanent, in such a way that at least said withholding element is disposable.

6. The biopsy needle according to claim 5, wherein said extension has side walls designed to contain the tissue specimen laterally.

7. The biopsy needle according to claim 1, wherein said extension has side walls designed to contain the tissue specimen laterally.

8. The biopsy needle according to claim 1, wherein the external cannula has a polygonal cross section.

9. The biopsy needle according to claim 1, wherein the external cannula has a rounded cross section.

10. The biopsy needle according to at least claim 1, further comprising a sliding element designed to be set in contrast with the extension to re-open said extension so as to facilitate extraction of the tissue specimen without damaging the specimen.

11. The biopsy needle according to claim 1 and adapted for taking intra-osseous samples, wherein the cannula has a penetrating end which is truncated at right angles with respect to the axis of the needle and is provided with a serrated edge, and wherein the closing stem has a faceted tip.

* * * * *